United States Patent
Frach

(10) Patent No.: US 11,079,501 B2
(45) Date of Patent: Aug. 3, 2021

(54) ADVANCED TEMPERATURE COMPENSATION AND CONTROL CIRCUIT FOR SINGLE PHOTON COUNTERS

(71) Applicant: KONINKLIJKE PHILIPS N.V., Eindhoven (NL)

(72) Inventor: Thomas Frach, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 282 days.

(21) Appl. No.: 16/239,609

(22) Filed: Jan. 4, 2019

(65) Prior Publication Data
US 2019/0137636 A1    May 9, 2019

Related U.S. Application Data

(63) Continuation of application No. 14/548,326, filed on Nov. 20, 2014, now abandoned, which is a continuation of application No. 13/148,055, filed as application No. PCT/IB2010/050539 on Feb. 5, 2010, now Pat. No. 8,921,754.

(Continued)

(51) Int. Cl.
| | |
|---|---|
| *G01T 1/24* | (2006.01) |
| *G01T 1/20* | (2006.01) |
| *G01T 7/00* | (2006.01) |
| *G01T 1/40* | (2006.01) |
| *A61B 6/03* | (2006.01) |

(52) U.S. Cl.
CPC .......... *G01T 1/247* (2013.01); *G01T 1/2018* (2013.01); *G01T 1/244* (2013.01); *G01T 1/248* (2013.01); *G01T 1/40* (2013.01); *G01T 7/005* (2013.01); *A61B 6/037* (2013.01)

(58) Field of Classification Search
CPC ....... A61B 6/037; G01T 1/2018; G01T 1/244; G01T 1/247; G01T 1/248; G01T 1/40; G01T 7/005
See application file for complete search history.

(56) References Cited

U.S. PATENT DOCUMENTS

| | | |
|---|---|---|
| 4,599,527 A | 7/1986 | Beaudet |
| 6,075,595 A | 6/2000 | Malinen |

(Continued)

OTHER PUBLICATIONS

Zappa, et al., "An integrated Active-Quenching Circuit for Single-Photon Avalanche Diodes", IEEE Transactions on Instrumentation and Measurement, vol. 49, No. 6, Dec. 2000.

(Continued)

*Primary Examiner* — Blake C Riddick

(57) ABSTRACT

A PET scanner includes a ring of detector modules encircling an imaging region. Each of the detector modules includes one or more sensor avalanche photodiodes (APDs) that are biased in a breakdown region in a Geiger mode. The sensor APDs output pulses in response to light from a scintillator corresponding to incident photons. A reference APD also biased in a breakdown region in a Geiger mode is optically shielded from light and outputs a voltage that is measured by an analog to digital converter. Based on the measurement, a bias control feedback loop directs a variable voltage generator to adjust a bias voltage applied to the APDs such that a difference between a voltage of a breakdown pulse and a preselected logic voltage level is minimized.

20 Claims, 7 Drawing Sheets

Related U.S. Application Data

(60) Provisional application No. 61/157,923, filed on Mar. 6, 2009.

(56) References Cited

U.S. PATENT DOCUMENTS

| | | |
|---|---|---|
| 6,222,660 B1 | 4/2001 | Traa |
| 6,313,459 B1 | 11/2001 | Holfe |
| 6,570,149 B2 | 5/2003 | Maruyama |
| 6,858,829 B2 | 2/2005 | Nishimura |
| 7,155,133 B2 | 12/2006 | Stewart |
| 7,217,914 B2 | 5/2007 | Stewart |
| 7,402,788 B2 | 7/2008 | McVey |
| 7,332,702 B2 | 12/2008 | Nishiyama |
| 7,723,694 B2 | 5/2010 | Frach |
| 7,800,070 B2 | 9/2010 | Weinberg |
| 7,847,553 B2 | 12/2010 | Schon |
| 8,395,127 B1 | 3/2013 | Frach |
| 8,399,848 B2 | 3/2013 | Frach |
| 2001/0023944 A1 | 9/2001 | Maruyama |
| 2005/0012033 A1* | 1/2005 | Stern ............... G01T 1/2928 250/214 R |
| 2007/0237465 A1* | 10/2007 | Okada ............... G02B 6/4246 385/92 |
| 2008/0156993 A1 | 7/2008 | Weinberg |
| 2009/0140153 A1* | 6/2009 | Flamanc ............. G01T 1/2018 250/368 |
| 2009/0309648 A1* | 12/2009 | Zheng ............... H01L 31/107 327/514 |

OTHER PUBLICATIONS

Scafe, et al., "Scintillation crystal readout by multi-APD for event localization", Nuclear Instruments and Methods in Physics Research; A 569; 2006.

Horste, et al., "Adjusting APD power-supply voltage with DACs and variable resistors", Lightwave; 2007; http:lw.pennet.com/display_article/305881/13/ARTCL/none/none/1.

* cited by examiner

ADVANCED TEMPERATURE COMPENSATION AND CONTROL CIRCUIT FOR SINGLE PHOTON COUNTERS

CROSS REFERENCE TO RELATED APPLICATIONS

This application is a continuation of U.S. application Ser. No. 14/548,326 filed Nov. 20, 2014, which is a continuation of U.S. application Ser. No. 13/148,055 filed Aug. 5, 2011, now U.S. Pat. No. 8,971,754, issued Dec. 30, 2014, which is a U.S. National Stage Entry of PCT Application Ser. No. PCT/IB2010/050539, filed Feb. 5, 2010, published as WO 2010/100574 A2 on Sep. 10, 2010, which claims the benefit of U.S. Provisional Application Ser. No. 61/157,923 filed Mar. 6, 2009, which is incorporated herein by reference.

DESCRIPTION

The following relates to the diagnostic imaging arts. It finds particular application in conjunction with radiation detectors for nuclear medical imagers employing radiation transmission or radiopharmaceuticals, such as single photon emission computed tomography (SPECT) imagers, positron emission tomography (PET) imagers, planar x-ray imagers, and the like, and will be described with particular reference thereto. It will be appreciated that the invention may also be applicable to other radiation imaging modalities, and in systems and methods employing radiation detectors such as astronomy and airport luggage screening.

In SPECT, a radiopharmaceutical is administered to an imaging subject, and one or more radiation detectors, commonly called gamma cameras, are used to detect the radiopharmaceutical via radiation emission caused by radioactive decay events. Typically, each gamma camera includes a radiation detector array and a honeycomb collimator disposed in front of the radiation detector array. The honeycomb collimator defines a linear or small-angle conical line of sight so that the detected radiation comprises projection data. If the gamma cameras are moved over a range of angular views, for example over a 180° or 360° angular range, then the resulting projection data can be reconstructed using filtered back-projection, expectation-maximization, or another imaging technique into an image of the radiopharmaceutical distribution in the imaging subject. Advantageously, the radiopharmaceutical can be designed to concentrate in selected tissues to provide preferential imaging of those selected tissues.

In PET, a radiopharmaceutical is administered to the imaging subject, in which the radioactive decay events of the radiopharmaceutical produce positrons. Each positron interacts with an electron to produce a matter/anti-matter annihilation event that emits two oppositely directed gamma rays. Using coincidence detection circuitry, an array of radiation detectors surrounding the imaging subject detects the coincident oppositely directed gamma ray events corresponding to the positron-electron annihilation. A line of response (LOR) connecting the two coincident detections contains the position of the positron-electron annihilation event. Such lines of response are analogous to projection data and can be reconstructed to produce a two- or three-dimensional image. In time-of-flight PET (TOF-PET), the small time difference between the detection of the two coincident γ ray events is used to localize the annihilation event along the LOR.

In planar x-ray imaging, a radiation source irradiates a subject, and a radiation detector array disposed on the opposite side of the subject detects the transmitted radiation. Due to attenuation of radiation by tissues in the imaging subject, the detected radiation provides a two-dimensional planar representation of bones or other hard, radiation-absorbing structures in the imaging subject. Such transmission-based imaging is improved upon in computed tomography (CT) imaging, in which the radiation source is revolved around the imaging subject to provide transmission views or projection data over an extended angular range, for example over a 180° or 360° span of angular views. Using filtered back-projection or another image reconstruction technique, this radiation projection data is reconstructed into a two- or three-dimensional image representation.

SPECT, PET, and other radiation-based medical imaging share a common need for compact and robust radiation detector modules. In the past, SPECT and PET radiation detector modules have typically consisted of an array of photomultiplier tubes (PMT's) optically coupled with scintillator crystals. The scintillator crystal absorbs the radiation particle and converts it into a light burst which is measured by the photomultiplier tubes. Photomultiplier tubes provide high detection and gain (~$10^6$) characteristics but they are bulky, fragile, require high voltages, and are very sensitive to magnetic fields. In some radiation detection systems, the photomultiplier tubes have been replaced by photodiodes that produce an analog signal proportional to the intensity of the light bursts. Even though photodiodes offer a cost-effective, low voltage alternative to photomultiplier tubes in high light situations, they do not provide the adequate gain in low light (low gamma ray flux) sensing applications, thus leading to poor signal-to-noise ratios.

To address these difficulties, silicon photomultiplier (SiPM) detectors have been developed that incorporate the high gain and stability of photomultiplier tubes along with the cost-effective, low voltage nature of the photodiodes. SiPM detectors use an array of small avalanche photodiodes (APDs) that are each optically coupled to a corresponding scintillation crystal. The APDs are biased in a breakdown region. In this region, the APDs become sensitive to single carriers, such as may be caused by an incident photon. These carriers, electrons and/or holes, can also be thermally generated, thus leading to dark counts that cause noise. Both electrons and holes can initiate the breakdown of the diode, thereby producing a strong output signal. In analog SiPMs, the output signal consists of the cumulative charge of a large number of passively quenched diodes. In contrast, digital SiPMs detect breakdown events individually based on voltage pulses that are digitized by logic gates and counted by digital counters that are located approximate to the APDs.

In digital Geiger-mode, APDs break down in response to a photon of light from a radiation event in the corresponding scintillation crystal and produce an output pulse. The output pulse functioning as binary 1's are counted to determine the number of photons generated by the radiation event striking the corresponding scintillator. This photon count corresponds to the energy of the detected radiation event.

While sensitive to individual photon events, breakdown voltage of each APD is affected by various ambient factors, such as magnetic fields and temperature. Drift of the breakdown voltage leads to a corresponding change of an excess voltage. Photon detection is affected by changes in excess voltage because: (1) the excess voltage determines the field strength inside the device, thus leading to a drift of the photon detection probability, and (2) the charge pulse produced during breakdown is proportional to the product of the diode capacitance and the excess voltage. Analog SiPMs, which count detected photons as a measured charge signal, are affected by both factors and become very sensitive to ambient conditions. The dark current rate (DCR) is doubled approximately every 8° C. To reduce the DCR of the sensor and avoid errors due to variations in the APDs, cooling can help, but even with cooling, temperature fluctuations can occur.

The present application contemplates a new and improved nuclear imaging detector apparatus and method that overcomes the above-referenced problems and others.

In accordance with one aspect, a radiation detector module is provided. A plurality of detector pixels each have a scintillator optically coupled to at least one sensor photodiode operated in a Geiger mode. At least one reference photodiode is shielded from light and is operated under the same conditions as the at least one sensor photodiode. The module includes a control circuit that measures a breakdown voltage across the reference photodiode, and adjusts a bias voltage across the at least one reference photodiode and the at least one sensor photodiode. This brings the dark current pulses generated by the at least one reference photodiode into substantial equality with the characteristic logic voltage level.

In accordance with another aspect, a method of compensating for drift in a sensitivity of a portion of a radiation detector array is provided. A bias voltage is applied to a plurality of sensor photodiodes and a parallel connected reference photodiode. The reference photodiode is covered with an opaque covering, preventing it from receiving light from an associated scintillator. The bias voltage biases the photodiodes to a Geiger mode, sensitive to single photons. Following breakdown of the reference photodiode, a breakdown voltage of the reference photodiode is measured. A difference between a value of a digitized pulse from the reference photodiode and a logic voltage level is determined. The bias voltage is adjusted to minimize the difference.

One advantage resides in improved breakdown voltage control for avalanche photodiodes operated in the Geiger mode.

Another advantage lies in compensation for several ambient factors that affect the sensitivity of the photodiodes.

Another advantage lies in the flexibility to be used in either analog or digital systems.

Another advantage lies in the freedom of the system builder to relax requirements on temperature stabilization without compromising system performance.

Still further advantages and benefits will become apparent to those of ordinary skill in the art upon reading and understanding the following detailed description.

The present application may take form in various components and arrangements of components, and in various steps and arrangements of steps. The drawings are only for purposes of illustrating the preferred embodiments and are not to be construed as limiting the present application.

Figure 1:
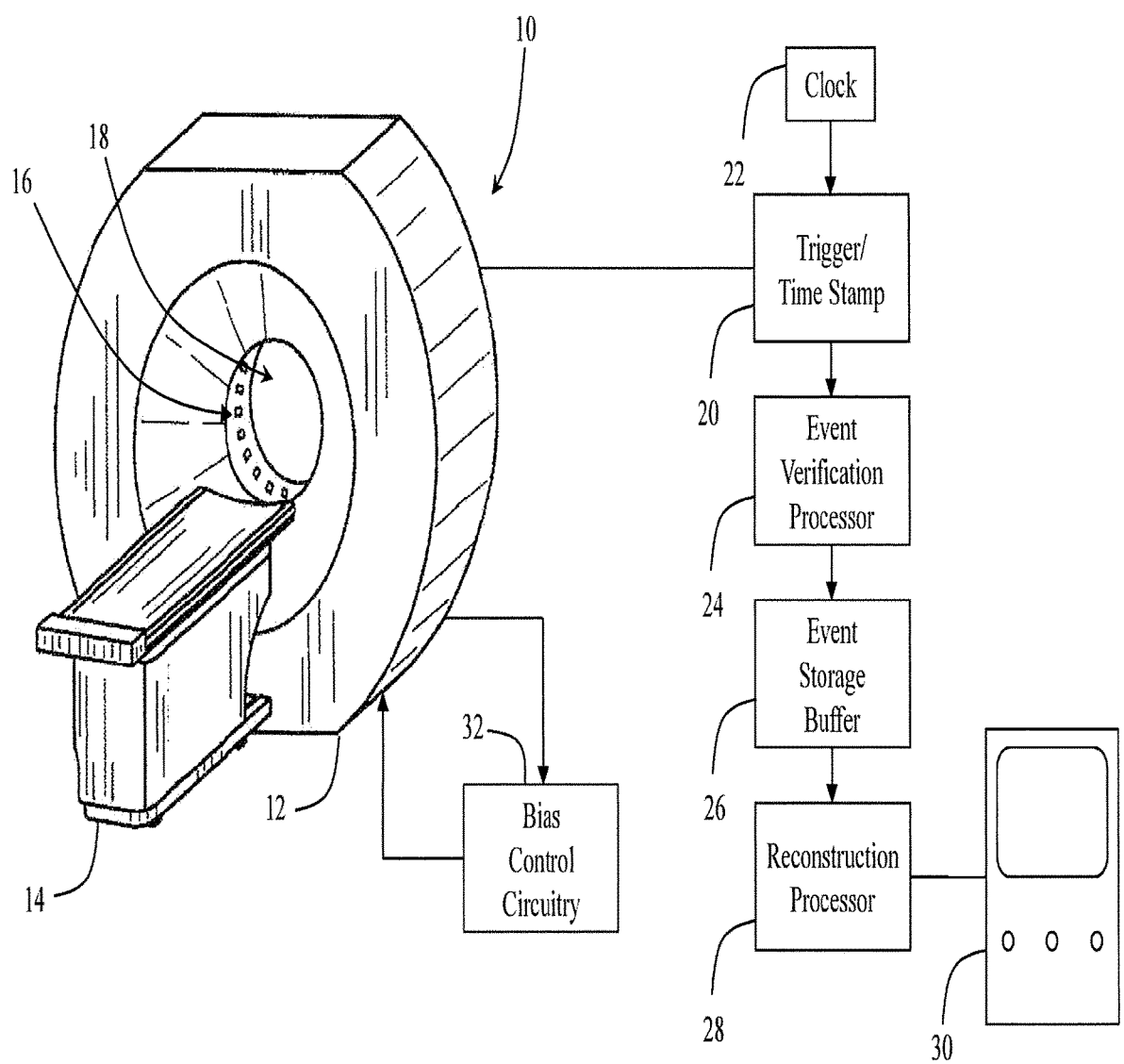
FIG. 1 is a diagrammatic illustration of a nuclear imaging scanner in accordance with the present application.

With reference to FIG. 1, a diagnostic imaging device 10 includes a housing 12 and a subject support 14. Enclosed within the housing 12 is a detector array. The detector array includes a plurality of individual detector modules 16. The array may include hundreds or thousands of radiation detector modules 16. While one particular embodiment is described with reference to a positron emission tomography (PET) scanner, it is to be understood that the present application is also useful in other medical applications, such as single photon emission computed tomography (SPECT) as well as x-ray astrophysics, gamma ray telescopes, radiography, security, and industrial applications. Generally, the present application finds use in imaging x-rays, gamma rays, or charged particles with high energy and spatial resolution. The array is arranged so that detector elements 16 are disposed adjacent to an imaging region 18 and oriented to receive radiation from the imaging region 18. The subject support 14 is movable in to and out of the imaging region 18. This allows the detector array to be sensitive to multiple views of the subject, without having to reposition the subject on the support 14. The detector array can be a ring of detectors 16, multiple rings, one or more discrete flat or arced panels, or the like.

In PET, pairs of gamma rays are produced by a positron annihilation event in the imaging region and travel in approximately opposite directions. Such an event may be produced from the nuclear decay of $^{82}$Rb. These gamma rays are detected as pairs, with a slight time difference (on the order of nanoseconds or fractions thereof) between detections if one gamma ray travels farther to reach a detector than the other. Accordingly, in PET scanners, the detector arrays typically encircle the imaging region.

Before the PET scan commences, a subject is injected with a radiopharmaceutical. In one common exam, the radiopharmaceutical contains a radioactive element, such as $^{82}$Rb, coupled to a tag molecule. The tag molecule is associated with the region to be imaged, and tends to gather there through body processes. For example, rapidly multiplying cancer cells tend to expend abnormally high amounts of energy duplicating themselves. The radiopharmaceutical can be linked to a molecule, such as glucose, or an analog thereof, that a cell typically metabolizes to create energy, which gathers in such regions and appear as "hot spots" in the image. Such a tag is also useful in cardiac perfusion imaging, since the heart expends relatively large amounts of energy. Other techniques monitor tagged molecules flowing in the circulatory system. In such a technique, it is beneficial to tag a molecule that is not quickly absorbed by tissues of the body.

When a gamma ray strikes the detector array, a time signal is generated. A triggering processor 20 monitors each detector 16 for an energy spike, e.g., integrated area under the pulse, characteristic of the energy of the gamma rays generated by the radiopharmaceutical. The triggering processor 20 checks a clock 22 and stamps each detected gamma ray with a time of leading edge receipt stamp. The time stamp, energy estimate and position estimation is first used by an event verification processor 24 to determine if the event data is valid, e.g., if the pair of events are coincident, have the proper energy, and the like. Accepted pairs define lines of response (LORs). Because gamma rays travel at the speed of light, if detected gamma rays arrive more than several nanoseconds apart, they probably were not generated by the same annihilation event and are usually discarded. Timing is especially important in time of flight PET (TOF-PET), as the minute difference in substantially simultaneous coincident events is used to further localize the annihilation event along the LOR. As the temporal resolution of events becomes more precise, so too does the accuracy with which an event can be localized along its LOR.

LORs are stored in an event storage buffer 26. In one embodiment, the LORs are stored in a list-mode format. That is, the events are stored in temporal order with time indicators periodically inserted. Alternatively, the events can be individually time stamped. A reconstruction processor 28 reconstructs all or a portion of the LORs into an image representation of the subject using filtered backprojection or other appropriate reconstruction algorithms. The reconstruction can then be displayed for a user on a display device 30, printed, saved for later use, and the like.

Each detector module 16 includes a plurality of photodiodes in one embodiment. While operating the photodiodes in Gieger mode, a reverse bias voltage is applied to allow the photodiodes to be sensitive to single photons of light generated by associated scintillation crystals optically coupled to the photodiodes. The scintillators are selected to provide high stopping power for incumbent radiation with rapid temporal decay of the scintillation burst. Some suitable scintillator materials include LSO, LYSO, MLS, LGSO, LaBr, CsI(Ti), and mixtures thereof. The bias voltage is applied such that the photodiodes produce an avalanche current when struck by the scintillated photons, earning them the moniker avalanche photodiodes (APDs). The optimum bias voltage is sensitive to multiple factors, such as temperature, pressure, ambient light, and the like. Bias, voltage control circuitry 32 monitors the detector modules 16 and adjusts the applied bias voltage as conditions dictate.

Figure 2:
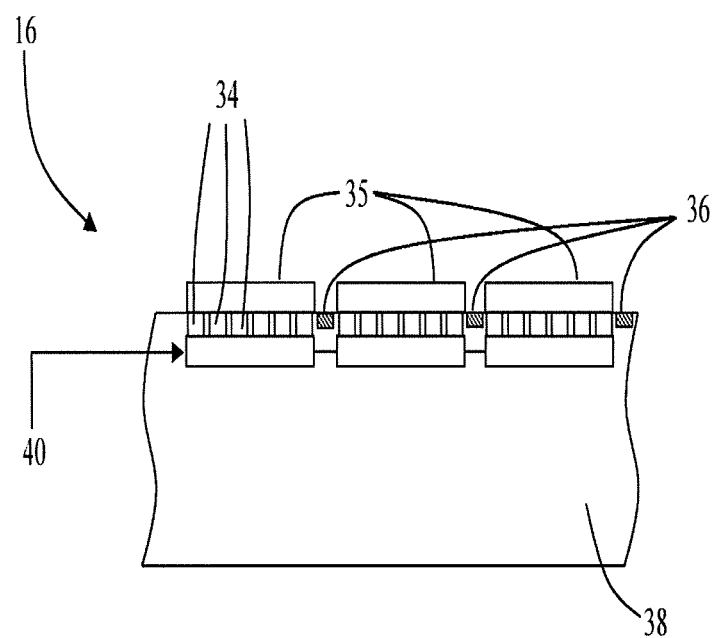
FIG. 2 depicts a cutaway view of a detector module, in accordance with the present application.

With reference to FIG. 2, a pixelated detector module 16 includes at least one sensor APD 34, more particularly one or more SiPMs each including an array of the APDs 34, optically coupled to a scintillation crystal 35. Additionally, each module 16 also includes at least one reference detector 36, such as a reference APD. The reference APDs 36 are covered with an opaque enclosure, such as a metal cap, to prevent light (ambient light or scintillation bursts) from reaching the reference APDs 36. The reference APDs 36 are placed among the sensor APDs 34, as it is desirable to have the sensor APDs 34 and the reference APDs 36 operating in the same environment, aside from the reception of light. In the illustrated embodiment, the sensor APDs 34 and reference APDs 36 are formed on a common substrate 38.

A digital circuitry layer 40 is electronically connected to the sensor photodiodes 34 and the reference photodiodes 36. The digital circuitry layer 40 includes circuitry that collects and outputs photon detection specific information such as radiation detector module identification, pixel identification, timestamps, and photon counts. The digital circuitry may also include digital biasing circuitry, digital triggering circuitry, and readout circuitry. The bias control circuitry 32 can be located in the digital circuit layer 40. Alternately, the bias control circuitry 32 can be located on a separate chip or die.

Figure 3:
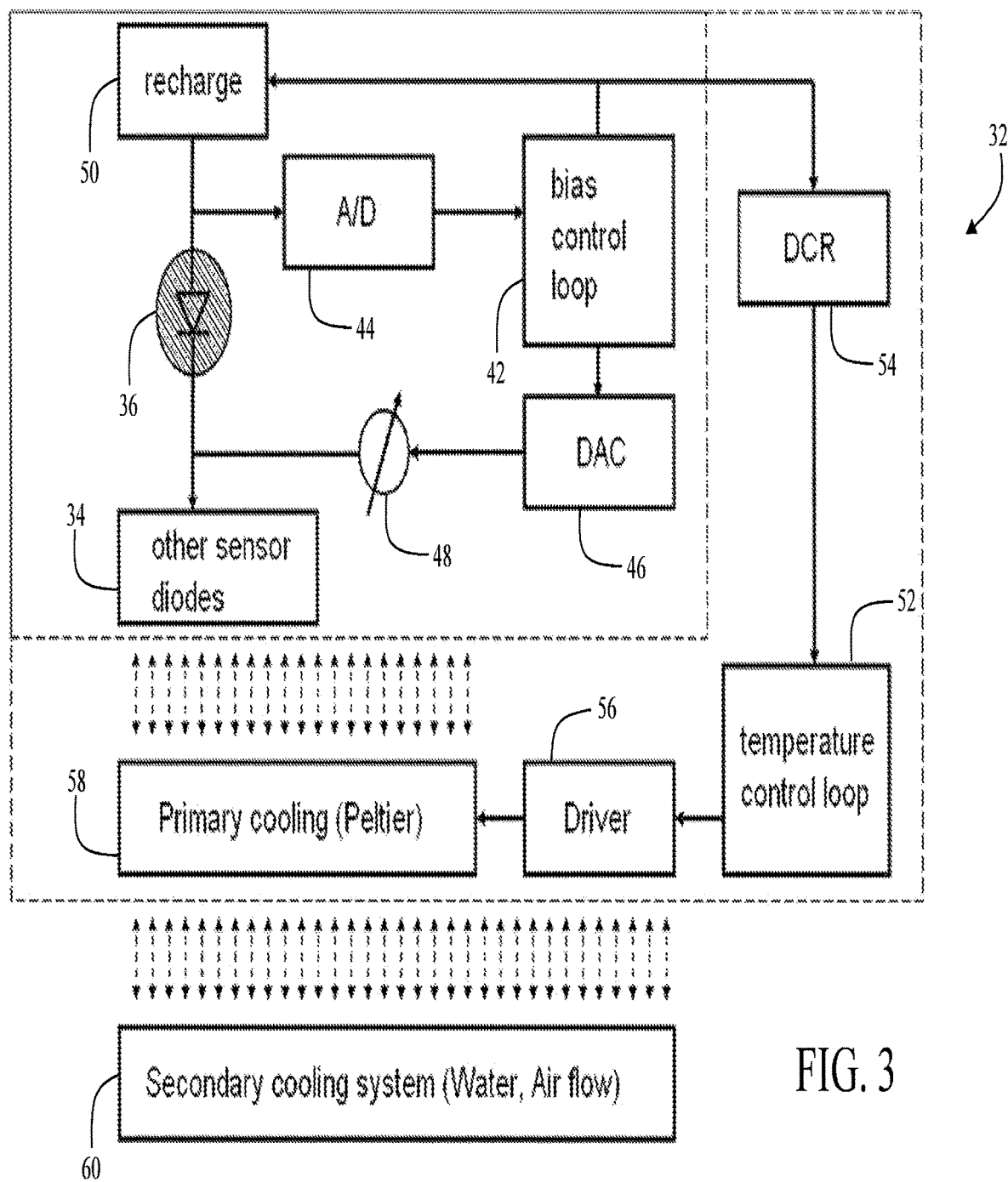
FIG. 3 is a flow diagram depicting bias control and temperature control feedback loops.

With reference now to FIG. 3, the bias control circuitry 32 includes a first, bias control feedback loop 42. Instead of detecting photo-generated electron-hole pairs, the reference APD 36 detects thermally generated electron-hole pairs or dark current. Thermally generated electron-hole pairs are created by generation-recombination processes within the semiconductor and can trigger an avalanche current in the absence of scintillated photons, producing noise in the system. The bias voltage across the APDs 34, 36 can be adjusted to make the APDs 34, 36 more or less sensitive, commensurate with the ambient surroundings.

When the reference APD 36 breaks down, an analog-to-digital converter (ADC) 44 converts the resulting anode voltage into a digital value, equivalent to the breakdown voltage. The AD converter converts the anode voltage after the avalanche current has decayed through the diode (there is no current flowing outside the diode during the breakdown). The current inside the diode discharges the diode capacitance and thus leads to a voltage drop at the anode (the cathode is pinned to a fixed voltage level, while the anode is left floating by leaving the reset transistor open). The internal current stops flowing when the voltage over the diode has reached the breakdown voltage, below that voltage, there is no multiplication possible and therefore most of the current stops and only a tiny leakage current continues to discharge the diode. The signal is processed and changed back into an analog signal by a digital-to-analog converter (DAC) 46, and is used to adjust a variable voltage source 48 that reverse biases the sensor APDs 34 and the reference APDs 36. The avalanche current, which is in the order of $10^6$ electrons per photon, will continue to flow until the voltage over the diode has reached the breakdown voltage. The time for this to happen is typically 200-300 ps depending on the excess voltage, diode capacitance and internal resistance. After that, there is no current flowing and the anode voltage reflects the breakdown voltage. This steady-state anode voltage is measured by the AD converter and the bias voltage is adjusted so that the anode voltage equals the logic level. A recharge transistor 50 is used to charge the diode back above the breakdown voltage for the next measurement cycle. That recharge pulse is about 10-15 ns long while the time to the next discharge can be in the millisecond range. A more detailed discussion of the bias control loop 42 is undertaken hereinbelow, in reference to FIG. 4.

With continuing reference to FIG. 3, a second, temperature control loop 52 is illustrated. The digital pulses from the ADC 44 are counted by a dark pulse counter 54 within a predetermined time period. Alternately, the dark pulse counter 54 could detect and count the activity of the recharging circuit 50. The dark pulse counter 54 outputs a digital value representative of the dark count rate. As temperature is proportional to the dark count rate, a driver 56 uses the dark count rate to drive a primary temperature control element 58, such as a Peltier cooling element, to quickly fine-tune the operating temperature of the APDs 34, 36. A secondary cooling element 60, which can use water, air, or other coolants, can be used to remove heat from the system. Limiting temperature variance is desirable to to limit the variance of the temperature in order to always get the same number of counts per photon.

Figure 4:
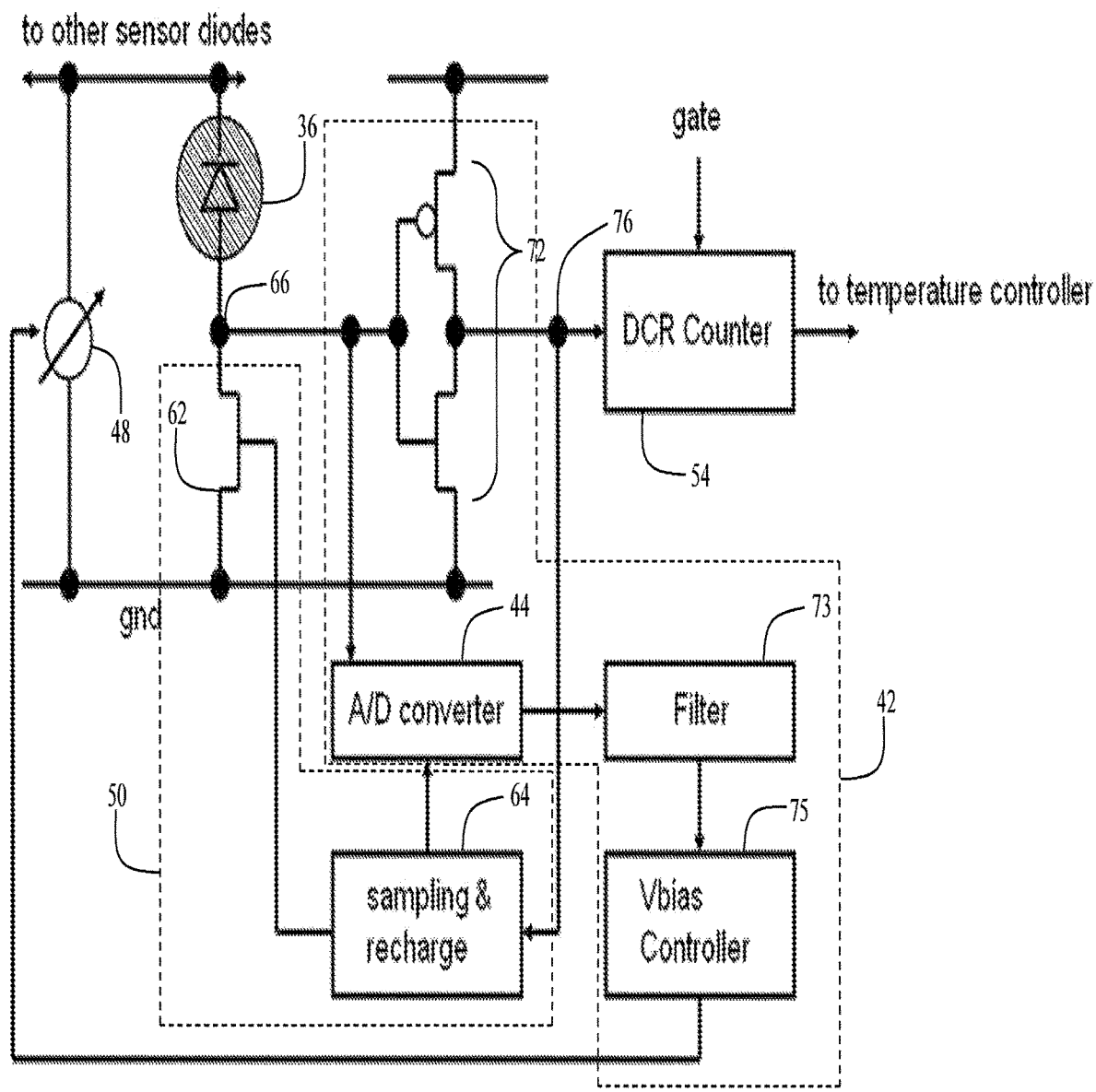
FIG. 4 shows certain circuit components used to realize the feedback loops of FIG. 3.
Figure 5:
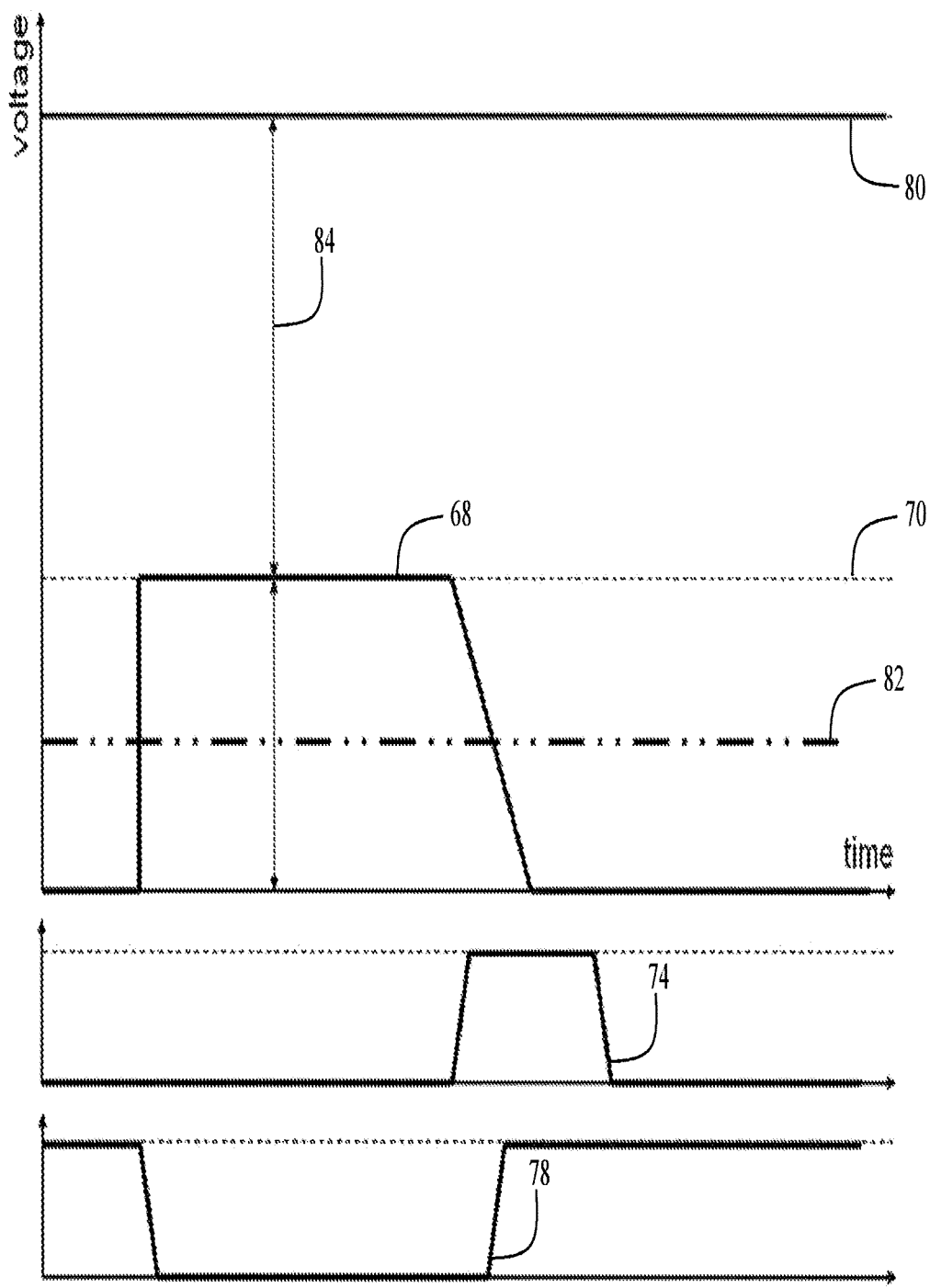
FIG. 5 depicts waveforms detailing one cycle of the circuits of FIGS. 3 and 4, with an accurate bias voltage.

With reference now to FIG. 4, the reference APD 36 is reverse biased with the variable voltage source 48. The anode is connected to a transistor 62 that is used to recharge the reference APD 36 to a selected voltage over the reference APD's 36 breakdown voltage. This is done by applying a short pulse to the gate of the transistor 62 with sampling and recharge circuitry 64, allowing the transistor 62 to turn it conductive. In one embodiment, the transistor 62 is an NMOS transistor. After this recharge, the reference APD 36 is left sensitive to carriers and will eventually break down. With reference to FIG. 5 and continuing reference to FIG. 4, during breakdown, the voltage at node 66 increases rapidly from zero, forming a voltage pulse 68, to a voltage dictated by the current operating conditions of the module 16. It is desirable for this voltage to be as close to a logic voltage level 70 as possible. The voltage pulse 68 is sensed by an inverter 72, which digitizes and passes the signal to the sampling and recharge circuitry 64, and the dark rate counter 54. The sampling and recharge circuitry 64 starts the ADC 44 to measure the actual voltage after the pulse 68 over the broken-down reference APD 36. Once the measurement is complete, the measurement is filtered 73 and passed to the bias voltage control feedback loop 42. More specifically, a bias voltage controller 75 controls the voltage output of the variable voltage source 48, described in more detail below. Additionally, the sampling and recharge circuitry 64 applies a pulse 74 that recharges the reference APD 36 resetting it so that it is once again sensitive to carriers. While the reference diode 36 is broken down, the voltage at node 76 drops to zero, as indicated by the waveform 78.

If the voltage pulse 68 is equal to the logic voltage level 70, then the bias voltage 80 is on target. Thus, a bias voltage control signal 82 produced by the bias control feedback loop 42 is correct, that is, half of the logic voltage level 70. If the bias voltage 80 is on target, no corrections are needed.

Figure 6:
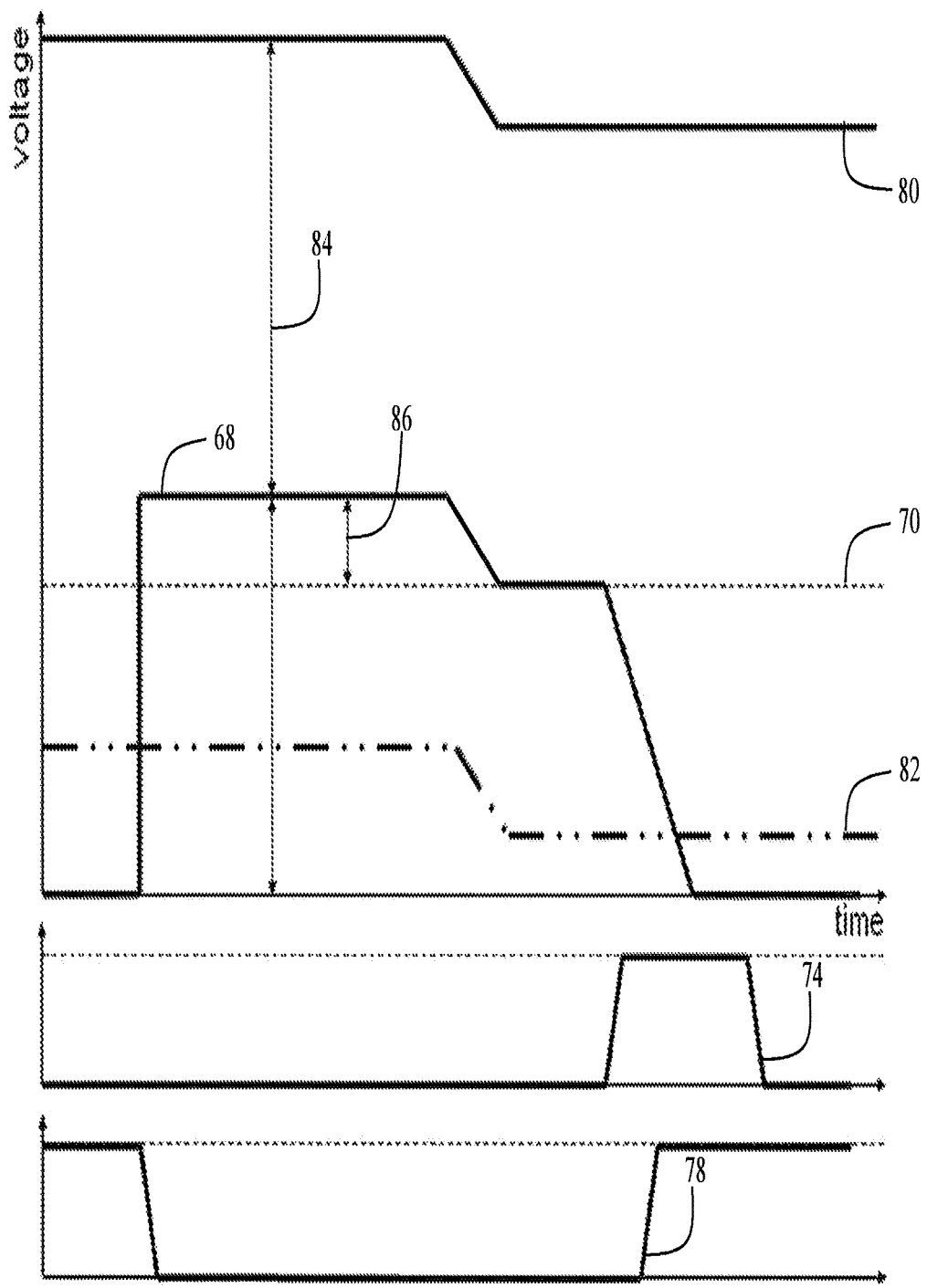
FIG. 6 depicts waveforms detailing one cycle of the circuits of FIGS. 3 and 4, with a bias voltage that is too high.

FIG. 6 depicts a situation in which the bias voltage 80 is too high, and is corrected. Such a situation may be caused by a shift in the breakdown voltage 84 of the APDs 34, 36 brought about, for example, by a lower ambient temperature. In this case, the voltage measured by the ADC 44 (i.e. the voltage of pulse 68) exceeds the logic voltage level 70 by a difference 86. In this situation, the bias control feedback loop 42 directs the variable voltage source 48 to lower the bias voltage 80, thus minimizing the difference 86 between the voltage pulse 68 and the logic voltage level 70. As in the previous example of FIG. 5, the sampling and recharge circuitry 64 applies the pulse 74 resetting the reference APD 36.

Figure 7:
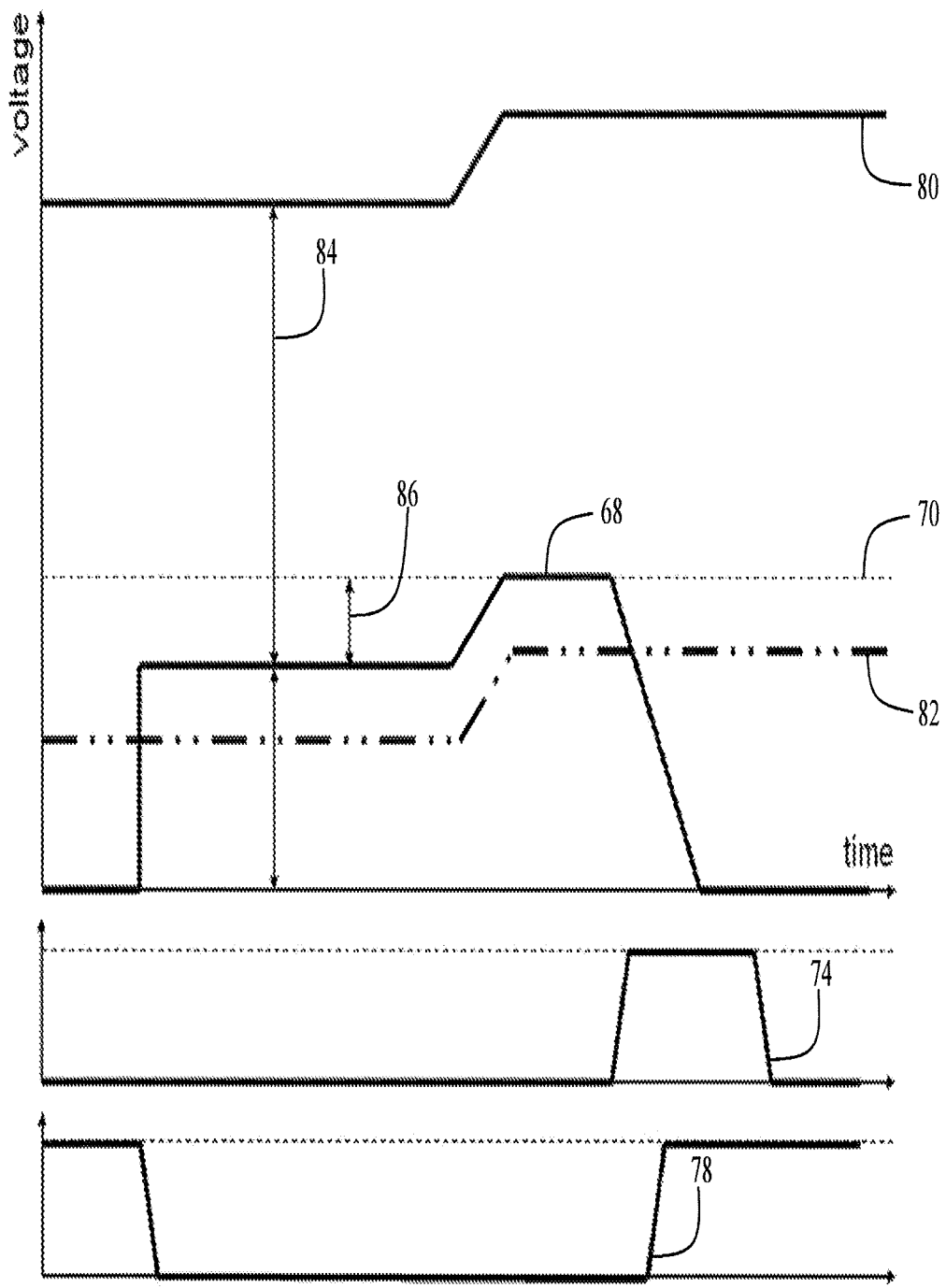
FIG. 7 depicts waveforms detailing one cycle of the circuits of FIGS. 3 and 4, with a bias voltage that is too low.

Similarly, FIG. 7 depicts a situation in which the bias voltage 80 is too low. Such a situation may be caused by a higher ambient temperature. In this case, the voltage measured by the ADC 44 (i.e. the voltage of pulse 68) is less than the logic voltage level 70 by the difference 86, which is now a negative value. In this situation, the bias control feedback loop 42 directs the variable voltage source 48 to raise the bias voltage 80, again minimizing the difference 86 between the voltage pulse 68 and the logic voltage level 70. Again, the sampling and recharge circuitry 64 applies the pulse 74 resetting the reference APD 36. In the illustrated embodiments, the bias voltage correction is done while the reference APD 36 is in its broken-down state. This allows the ADC 44 to monitor the difference 86 in real time.

In one embodiment, the circuitry depicted in FIGS. 3 and 4 can be integrated on the same die next to the APDs 34, 36 if the bias voltage is generated by a charge pump on the chip and enough chip area is available. Parts of the circuitry can be located on separate chips, thus allowing application in conjunction with analog silicon photomultipliers.

In an alternate embodiment, the bias control loop 42 can be implemented in a purely analog way, eliminating the ADC 44 and the DAC 46. In this embodiment, the reference photodiode 36 is operated at the breakdown voltage by impressing a well defined current (about 1 µA) and using the resulting voltage as a control signal for the variable voltage source 48. This embodiment would have the advantage of making the overall circuit more compact. In the digital embodiments, the ADC 44 can also be re-used to monitor other voltages. This can be useful for functional and parametric testing at the wafer level, and during the power-on sequence of the sensor module.

The present application has been described with reference to the preferred embodiments. Modifications and alterations may occur to others upon reading and understanding the preceding detailed description. It is intended that the present application be construed as including all such modifications and alterations insofar as they come within the scope of the appended claims or the equivalents thereof.

The invention claimed is:

1. A radiation detector for use in imaging comprising:
   a plurality of avalanche photodiodes including (1) at least one reference avalanche photodiode which is shielded from light and (2) a plurality of non-shielded avalanche photodiodes configured to receive light photons to be counted;
   a biasing circuit configured to bias the plurality of avalanche photodiodes to operate in a Geiger mode in which the at least one reference avalanche photodiode breaks down in response to dark currents and the non-shielded avalanche photodiodes breakdown in response to the dark currents and to receive light photons generating output pulses wherein the biasing circuit is configured to bias each of the plurality of avalanche photodiodes back to the Geiger mode after each breakdown;
   a first cooling element thermally coupled to the plurality of avalanche photodiodes and configured to remove heat from the plurality of avalanche photodiodes;
   a control circuit configured to count the output pulses generated by the at least one reference avalanche photodiode in response to the dark currents and control the first cooling element in accordance with a rate at which the output pulses from the shielded reference avalanche photodiode are counted.

2. The radiation detector as set forth in claim 1, wherein the control circuit is further configured to measure a breakdown voltage across at least the at least one reference avalanche photodiode and adjust the bias voltage of the plurality of avalanche photodiodes to a predetermined characteristic logic voltage level.

3. The radiation detector as set forth in claim 1, wherein the first cooling element includes a Peltier cooling element which is electrically controlled by the controller and further including:
   a second cooling element which transfers heat from the Peltier cooling element to ambient surroundings.

4. An imaging apparatus comprising:
   a gantry defining an imaging region;
   a subject support configured to support a subject in the imaging region;
   a detector array that includes a plurality of radiation detectors as set forth in claim 1;
   an event verification processor configured to analyze detected radiation to determine whether the detected radiation originated from valid events;
   a reconstruction processor configured to reconstruct the valid events into an image representation.

5. The radiation detector as set forth in claim 1, wherein a cathode of each of the plurality of avalanche photodiodes is pinned to a bias voltage and an anode of each of the plurality of avalanche photodiodes is floating, and during a breakdown, current flows from the cathode to the anode of the avalanche photodiode which broke down raising a voltage at the anode until the voltage at the anode reaches the bias voltage, and
   wherein in response to reaching the bias voltage, the biasing circuit is configured to bias the avalanche photodiode which broke down back to the Geiger mode.

6. The radiation detector as set forth in claim 5, wherein the breakdown raises the voltage at the anode to the bias voltage and biases the avalanche photodiode which broke down to zero such that the output pulse in response to each breakdown is of a selected common voltage.

7. The radiation detector as set forth in claim 1, wherein the control circuit includes two feedback paths, a first feedback path configured to control the bias voltage to bring the output voltage pulses of the reference and the non-shielded avalanche photodiodes to a preselected voltage level and a second feedback path configured to control the first cooling element.

8. The radiation detector as set forth in claim 1, wherein:
the non-shielded avalanche photodiodes are configured to be connected with a scintillator configured to emit the light photons received by the non-shielded avalanche photodiodes, the non-shielded avalanche photodiodes generating output pulses in response to the light photons and dark currents; and
the at least one shielded reference avalanche photodiode is configured to generate the output pulses in response to dark currents while the non-shielded avalanche photodiodes are generating the output pulses in response to the light photons and the dark currents.

9. The radiation detector as set forth in claim 1, wherein the control circuit includes two feedback paths, a first feedback path configured to control a magnitude of the output pulse to an amplitude indicative of a logic 1 and a second feedback path configured to control the cooling element to control the rate of the dark currents in the plurality of avalanche photodiodes.

10. The radiation detector as set forth in claim 9, wherein the non-shielded avalanche photodiodes break down in response to light photons and dark currents and wherein the reference avalanche photodiode breaks down in response to a dark current and further including:
a recharge circuit configured to recharge the avalanche photodiodes in response to the breakdown of the reference avalanche photodiode.

11. The radiation detector as set forth in claim 1, wherein the at least one reference avalanche photodiode has a cathode connected to a bias voltage line and a floating anode, the output pulse being generated at the cathode; and
wherein the control circuit includes:
a first feedback circuit configured to control the bias voltage on the bias voltage line; and,
a second feedback circuit configured to control the cooling element.

12. The radiation detector as set forth in claim 11, further including:
a recharge circuit configured to connect the anode of the reference avalanche photodiode to ground in response to each reference avalanche photodiode output pulse to bias the shielded reference avalanche photodiode back to the Geiger mode.

13. The radiation detector as set forth in claim 11, wherein the breakdown of each avalanche photodiode causes an avalanche current flowing from the cathode to the anode to raise a voltage at the anode toward the bias voltage, the avalanche current stopping when the anode voltage is raised substantially to the bias voltage such that the voltage at an output at the anode rises toward the bias voltage during the avalanche current, and further including a recharge circuit which, in response to the output voltage substantially reaching the bias voltage, is configured to connect the anode with a ground line such that the output becomes low;
wherein the control circuit is configured to adjust the bias voltage based on an amplitude of the output voltage such that the amplitude of the output voltage has a preselected amplitude indicative of a logic 1.

14. A radiation detector for use in imaging comprising:
a plurality of avalanche photodiodes, at least one of the avalanche photodiodes being a reference photodiode which is shielded from light;
a biasing circuit configured to bias the avalanche photodiodes to operate in a Geiger mode in which the avalanche photodiodes breakdown in response to receiving radiation generating an output pulse and the biasing circuit being configured to bias each photodiode back to the Geiger mode after each breakdown;
a first cooling element thermally coupled to the photodiodes and configured to remove heat from the photodiodes;
a control circuit configured to:
measure a breakdown voltage across the at least one reference photodiode and adjust the bias voltage of the photodiodes to a predetermined characteristic logic voltage level,
measure the breakdowns of the at least one reference photodiode and
control the first cooling element in accordance with a rate of the output pulses from the at least one shielded avalanche photodiode.

15. The radiation detector as set forth in claim 14, wherein the biasing circuit is configured to bias the photodiodes such that each breakdown generates a voltage pulse of the characteristic logic voltage level.

16. The radiation detector as set forth in claim 14, wherein the reference avalanche photodiode includes an anode connected to a bias voltage line and a floating anode, the breakdown of the reference avalanche photodiode causing an avalanche current to flow from the cathode to the anode dropping the voltage across the reference avalanche photodiode and raising a voltage at the anode, the avalanche current stopping when the voltage at the anode is raised substantially to the bias voltage; and further including:
a recharge circuit which, in response to the voltage across the reference avalanche photodiode dropping, is configured to connect the cathode with a ground line to bias the avalanche photodiode back to the Geiger mode;
wherein the control circuit is configured to adjust the available voltage source to just the bias voltage on the bias voltage line to bring anode voltage at breakdown to the predetermined characteristic voltage level.

17. The radiation detector as set forth in claim 14, wherein a first plurality of the avalanche photodiodes are not shielded from light and wherein the first plurality of avalanche photodiodes break down in response to receiving radiation to generate the output pulses to be counted concurrently with at least one shielded photodiode breaking down to generate output pulses to control the first cooling element.

18. A radiation detector for use in imaging comprising:
a plurality of avalanche photodiodes, the plurality of avalanche photodiodes including:
a first plurality of avalanche photodiodes configured to be optically connected with a scintillator, the first plurality of avalanche photodiodes generating output voltage pulses (i) in response to light photons from the scintillator in response to incident radiation and (ii) in response to dark currents,
at least one shielded avalanche photodiode, the at least one shielded avalanche photodiodes being shielded from the light photons from the scintillator, the at least one shielded avalanche photodiode generating the output voltage pulses in response to dark currents, a biasing circuit configured to bias the avalanche photodiodes to operate in a Geiger mode in which (i) the first plurality of avalanche photodiodes breakdown in response to at least one of receiving the light photons from the scintillator and the dark currents, (ii) the at least one shielded avalanche photodiode breaks down in response to the dark currents, and (iii) each breakdown generates an output voltage pulse, wherein the biasing circuit is further configured to bias each of the first plurality of avalanche photodiodes and the at least one shielded avalanche photodiode back to the Geiger mode after each breakdown;

a cooling element thermally coupled to the first avalanche photodiodes and the at least one shielded avalanche photodiode, the cooling element being configured to remove heat from the first plurality of avalanche photodiodes and the at least one shielded avalanche photodiode;

a control circuit configured to count the breakdowns of the first plurality of avalanche photodiodes, the control circuit including two feedback paths, a first feedback path configured to control a bias voltage to the first and shielded avalanche photodiodes to bring the output voltage pulses to a preselected common voltage level and a second feedback path configured to control the cooling element in accordance with a rate of the counted breakdowns of the at least one shielded avalanche photodiode.

19. The radiation detector as set forth in claim 18, wherein the preselected common voltage level corresponds to a logic 1 of associated digital circuitry.

20. The radiation detector as set forth in claim 18, wherein the control circuit concurrently counts the breakdowns of the first plurality of avalanche photodiodes and concurrently controls the bias voltage to bring the output voltage pulses to the preselected common voltage level and concurrently controls the cooling element in accordance with the rate of counted breakdowns by the at least one shielded avalanche photodiode.

* * * * *